US006878109B2

(12) United States Patent
Yamaki et al.

(10) Patent No.: US 6,878,109 B2
(45) Date of Patent: Apr. 12, 2005

(54) LIGHT SOURCE DEVICE FOR AN ENDOSCOPE USING A DMD

(75) Inventors: Masahide Yamaki, Hachioji (JP); Seiichi Hosoda, Hino (JP); Shuhei Iizuka, Hachioji (JP); Katsuichi Imaizumi, Hino (JP); Masaki Terakubo, Sagamihara (JP); Takeaki Nakamura, Hino (JP); Hiroshi Ibe, Yokohama (JP); Manabu Yajima, Hino (JP)

(73) Assignee: Olympus Corporation, Tokyo (JP)

( * ) Notice: Subject to any disclaimer, the term of this patent is extended or adjusted under 35 U.S.C. 154(b) by 147 days.

(21) Appl. No.: 10/085,704

(22) Filed: Feb. 28, 2002

(65) Prior Publication Data

US 2002/0156349 A1 Oct. 24, 2002

(51) Int. Cl.[7] .................................................. A61B 1/06
(52) U.S. Cl. ........................ 600/180; 600/178; 600/181
(58) Field of Search ................................. 600/178, 180, 600/181; 348/68, 72, 74, 76; 362/282, 283, 296, 297

(56) References Cited

U.S. PATENT DOCUMENTS

2003/0076571 A1 * 4/2003 MacAulay et al. ......... 359/237

FOREIGN PATENT DOCUMENTS

| JP | 2001-59942 | * | 3/2001 |
| JP | 2001-221959 | * | 8/2001 |
| JP | 2001-0235686 | * | 8/2001 |

* cited by examiner

Primary Examiner—John P. Leubecker
(74) Attorney, Agent, or Firm—Scully, Scott, Murphy & Presser (57) ABSTRACT

An endoscope system comprising an endoscope which incorporates an imaging element together with an element for determining the type of the imaging element; a light source apparatus, which includes a DMD in a light path from a light source lamp, for determining incidence or non-incidence of the illuminating light from the light source lamp on a mirror; a CPU which determines the type of imaging element based on the information provided by the type determining element and detects a time required by the imaging element for charge reading based on the determination result; and a DMD control circuit which controls the DMD at a charge reading timing of the imaging element corresponding to the charge reading time detected by the CPU, the endoscope system making it possible to extend the exposure time to a maximum regardless of the type of the endoscope, by controlling the light shielding time of illuminating light in accordance with the type of the imaging element.

14 Claims, 8 Drawing Sheets

LIGHT SOURCE DEVICE FOR AN ENDOSCOPE USING A DMD

Japanese Patent Application No.2000-314330, filed in Japan on Oct. 13, 2000, is incorporated by this reference.

BACKGROUND OF THE INVENTION

1. Field of The Invention

This invention relates to a light source apparatus for providing illuminating light to an endoscope with an imaging element, and to an endoscope system which is related with the observation of a test site by providing illuminating light to an endoscope with an imaging element.

2. Related Art Statement

Currently, endoscope systems for medical applications are widely used among general practitioners. These medical endoscope systems are configured so as to allow one to observe various test sites including the digestive organs such as the esophagus, stomach, small intestine, large intestine, etc., or the lungs and the like. Moreover, these medical endoscope systems further allow one to apply, as needed, various treatments to the site using a treatment tool inserted through a treatment channel. Particularly in recent years, electronic endoscope systems incorporating as an imaging unit a solid-state imaging element such as a charge coupled device (CCD) have become widely used. The electronic endoscope system can present a motion picture as a monitoring image on a color monitor on a real-time basis. Because of this, the electronic endoscope system is also advantageous in that it exerts less strain on the operator of the endoscope.

The electronic endoscope system comprises an electronic endoscope consisting of a CCD placed at the tip of a slender insertion segment, a processor unit for processing image pickup signals, and a light source apparatus for providing illuminating light. The electronic endoscope can be detachably attached to the processor unit and light source apparatus. Accordingly, for a given electronic endoscope system, it is possible to attach various types of endoscope to a single processor unit and light source apparatus. Further, the electronic endoscope may contain, for example, CCDs having various numbers of pixels depending on the site to which the CCD is applied or for a given application. As for the CCD, the time required for charge reading varies depending on its type.

The CCD installed in the electronic endoscope may include, to reduce the size of its imaging element, a type in which the charge accumulating portion also serves as the charge transferring path. In such a type, the electronic endoscope system must interrupt illuminating light required for illuminating a test object during a period in which the charge of the CCD is read out, so that an image of the object is not formed on the CCD during this period.

An electronic endoscope system which sequentially radiates red, blue, and green light two-dimensionally onto an object to be imaged achieves this by rotating a filter plate in which a light shielding sector is inserted between adjacent color filters. Through this arrangement, the electronic endoscope system based on the sequential two-dimensional light radiation can interrupt the light during light shielding periods. The length of the light shielding period is determined in accordance with the CCD which requires the longest time for charge reading.

For the aforementioned electronic endoscope system, the time required for reading out charge varies depending on the type of solid-state imaging element, such as a CCD, of the imaging unit. Namely, the light shielding period required for an electronic endoscope system varies depending on the solid-state imaging element it employs.

However, the conventional electronic endoscope system has a fixed light shielding period, regardless of the type of electronic endoscope it employs. As a consequence, the conventional electronic endoscope system may have a redundant light shielding period, if it incorporates a solid-state imaging element comprising a small number of pixels in which a relatively short period is required for reading out charge. Consequently, the conventional electronic endoscope system cannot ensure a sufficiently intense light exposure if the test object is in the dark, which has been a problem.

OBJECT AND SUMMARY OF THE INVENTION

The object of this invention is to provide a light source apparatus that is able to securely extend the light exposure time to the utmost regardless of the type of electronic endoscope employed, i.e., regardless of the number of pixels contained in the imaging element or of the time required for charge reading, and an endoscope system incorporating such a light source apparatus.

The light source apparatus for providing illuminating light to the endoscope of this invention comprises:

a light source lamp for generating illuminating light;

a digital micromirror device having a plurality of micromirrors which receives illuminating light generated by the light source lamp and reflects it;

a light converging optical system which directs illuminating light reflected by the plurality of micromirrors to be incident on a light guide introduced in the endoscope; and a mirror control circuit which determines whether or not illuminating light should impinge on the light guide by altering the direction of illuminating light reflected by the plurality of micromirrors of the digital micromirrors device, based on an exposure time signal introduced in accordance with the type of an imaging element installed in the endoscope.

Further, the endoscope system for enabling endoscopic observation by providing illuminating light to the endoscope of this invention comprises:

a light source lamp for generating illuminating light;

a digital micromirror device having a plurality of micromirrors which receives illuminating light generated by the light source lamp and reflects it;

a light guide capable of transmitting illuminating light installed in the endoscope;

a light converging optical system which directs illuminating light reflected by the plurality of micromirrors of the digital micromirror device to be incident on the light guide;

an imaging element installed in the endoscope;

a circuit for determining the type of the imaging element;

a control signal generating circuit which generates an exposure time control signal responsible for adjusting the exposure time of the imaging element in accordance with the imaging element's type determined by said circuit; and a mirror control circuit which alters the direction of illuminating light reflected by the plurality of micromirrors of the digital micromirror device dependent on the exposure time control signal generated by the control signal generating circuit, thereby determining whether or not illuminating light should be incident on the light guide.

The above and other objects, features and advantages of the invention will become more clearly understood from the following description referring to the accompanying drawings.

DETAILED DESCRIPTION OF PREFERRED EMBODIMENTS

A first embodiment of the present invention will be described below with reference to the accompanying drawings.

Figure 1:
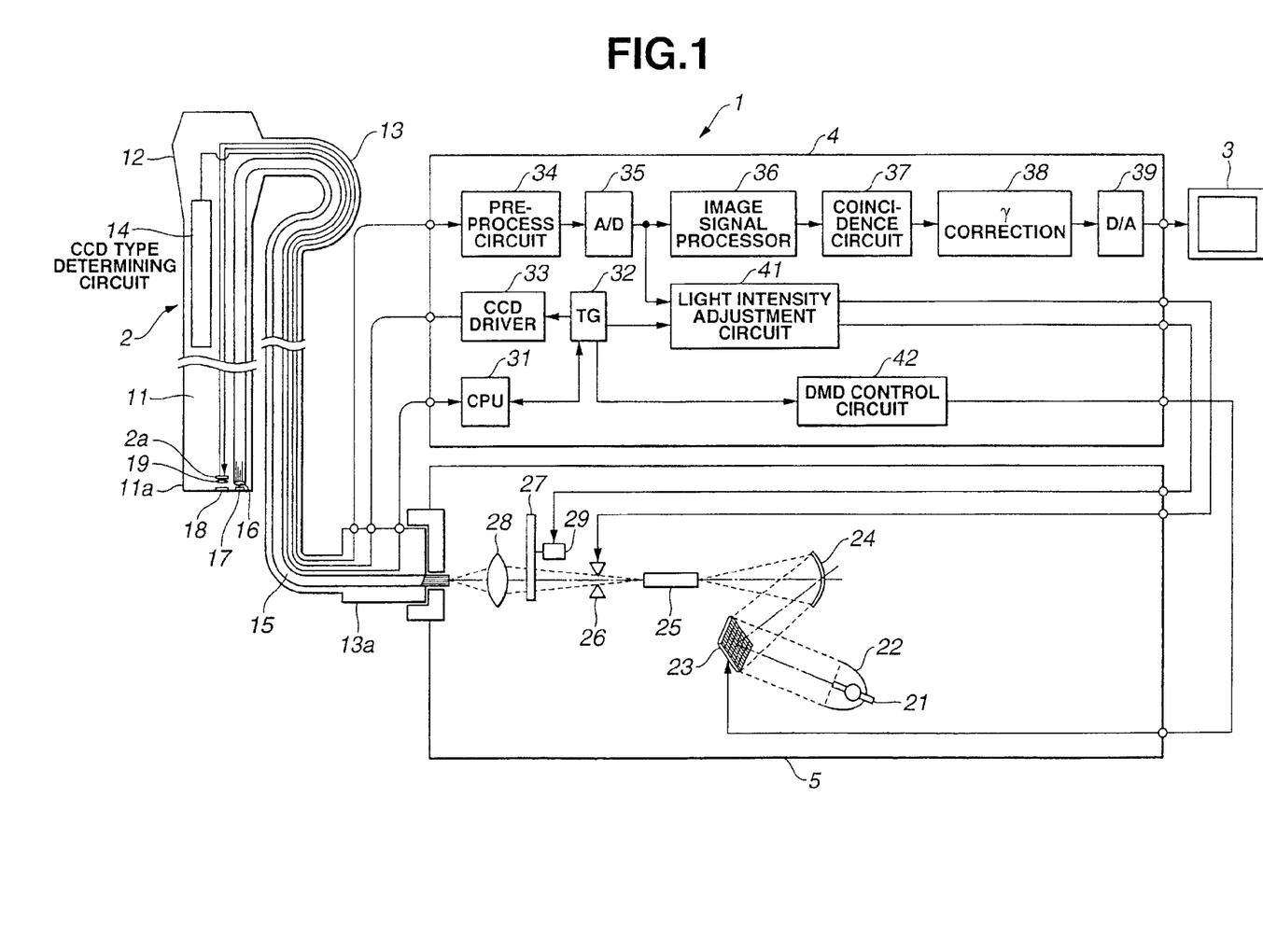
FIG. 1 is a diagram showing the construction of an endoscope system representing a first embodiment of the present invention.
Figure 2:
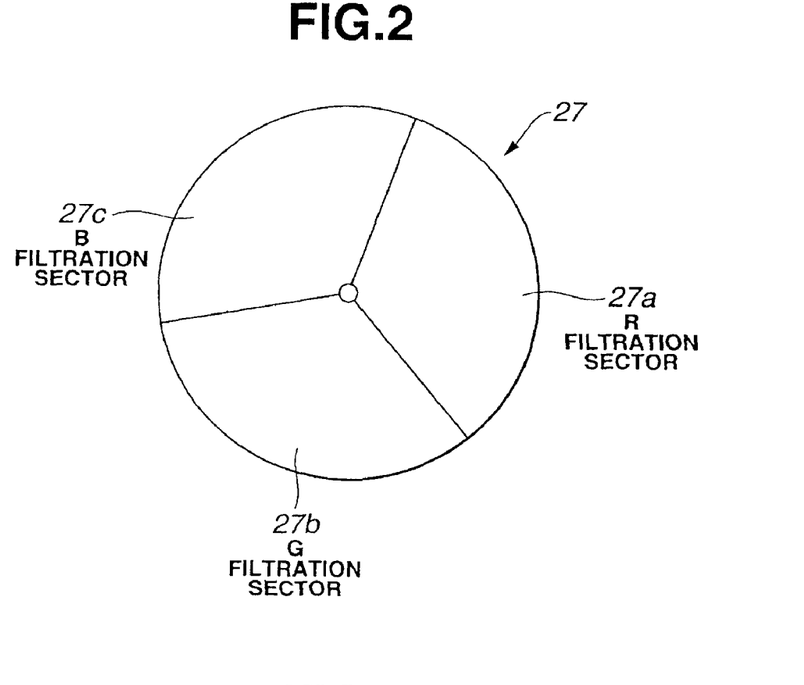
FIG. 2 is a diagram showing the configuration of a rotational filter plate of FIG. 1.
Figure 3:
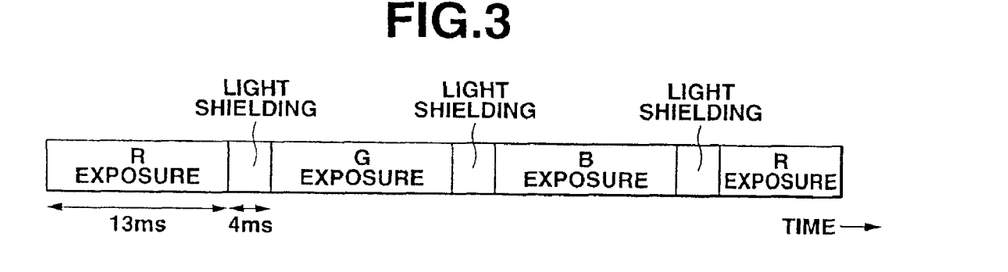
FIG. 3 illustrates how control by a DMD control circuit is introduced when a CCD in which a relatively short time is required for charge reading is employed.
Figure 4:
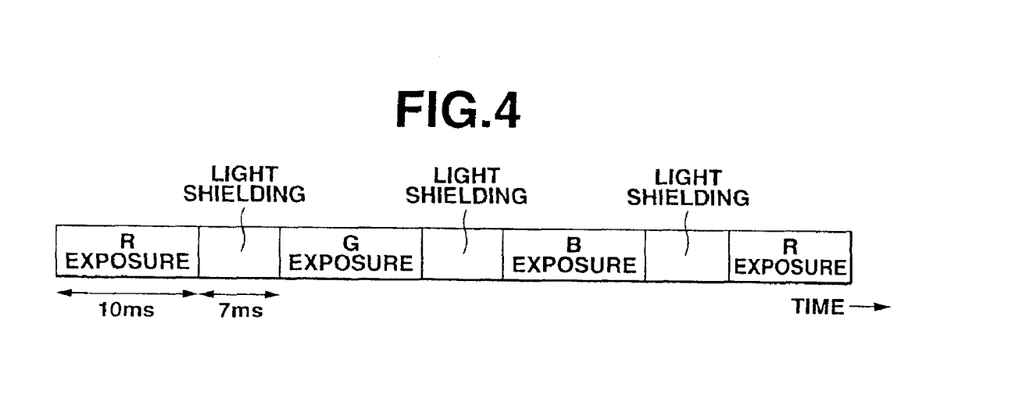
FIG. 4 illustrates how control by a DMD control circuit is introduced when a CCD in which a relatively long time is required for charge reading is employed.

FIGS. 1 to 4 are related to the first embodiment of the present invention: FIG. 1 is a diagram showing the construction of an endoscope system representing the first embodiment of the present invention; FIG. 2 is a diagram showing the configuration of a rotational filter plate of FIG. 1; FIG. 3 is an illustration showing how control by a DMD control circuit is introduced when a CCD in which a relatively short time is required for charge reading is employed; and FIG. 4 is an illustration showing how control by a DMD control circuit is introduced when a CCD in which a relatively long time is required for charge reading is employed.

As shown in FIG. 1, the endoscope system 1 representing the first embodiment of the present invention comprises an electronic endoscope 2 (to be referred to simply as an endoscope) incorporating a CCD 2a as an imaging unit; a video processor 4 for processing image pickup signals the CCD 2a of the endoscope 2 produced based on a test object, so as to allow a monitor 3 to display a monitoring image therefrom; and a light source apparatus 5 for providing illuminating light to the endoscope 2.

The endoscope 2 has a handle portion 12 at the base of a slender insertion segment 11. The endoscope 2 can be detachably attached to the light source apparatus 5 and the video processor 4 via a connector portion 13a at the terminal end of a universal cable 13 which extends from a side face of the handle portion 12 and which contains a light guide and the like, which are described later.

The endoscope 2 incorporates the CCD 2a at a tip 11a of the insertion segment 11. The endoscope 2 also incorporates, within the handle portion 12, a CCD type determining element 14 which stores information necessary for determining the type of the CCD 2a. The CCD-type determining element 14 may be attached to the connector portion 13a or introduced into the insertion segment 11.

The endoscope 2 has a light guide 15 inserted therethrough which extends from the tip 11a of the insertion segment 11 to the connector portion 13a of the universal cable 13 and is capable of conveying an image of a test object. Illuminating light generated by the light source apparatus 5 and transmitted via the light guide 15 is radiated onto a test object via an illumination lens 16 and an illumination cover glass 17. The endoscope 2 is configured such that an image of a test object, conveyed via an imaging cover class 18, can be focused via an objective optical system 19 on the imaging surface of the CCD 2a.

The optical system of the light source apparatus 5 comprises a light source lamp 21, such as a Xenon lamp, which radiates light to be provided to the endoscope 2; a parabolic mirror 22 which has its surface coated to filter out infra-red rays, so as to remove infra-red components from the light emanating from the light source lamp 21; a DMD (Digital Micromirror Device) 23 which interrupts the passage of parallel beams from the parabolic mirror 22 on a time axis; a reflection mirror 24 for reflecting a part of the radiation light radiated by the DMD 23; an integrator 25 for integrating beams reflected by the reflection mirror 24; an aperture 26 (referred to simply as aperture hereinafter) for reducing the intensity of illuminating light integrated by the integrator 25; a rotational filter plate 27 which filters beams having wavelengths corresponding to red, green, or blue out of the illuminating light whose intensity has been reduced by the aperture 26; and a converging lens 28 which converges beams having wavelengths corresponding to red, green, or blue, which were filtered by the rotational filter plate 27, onto a light-incident end surface of the light guide 15.

As shown in FIG. 2, the rotational filter 27 comprises an R filter sector 27a, a G filter sector 27b, and a B filter sector 27c which filter beams having wavelengths corresponding to red, green, and blue, respectively. The rotational filter 27 is driven into rotation by a motor 29.

The DMD 23 is an element obtained by arranging a matrix of 800×600 micromirrors each supported by a support member on a silicon chip over a yoke which moves about between two stable states, with one diagonal line as a pivot, so that the mirrors can move in a horizontal direction within an angular range of ±10° independently of each other. The DMD 23 is arranged with respect to incident light from the parabolic mirror 22 such that, if, for example, a micromirror is set to take an angle of −10°, illuminating light reflected by the mirror will impinge, via the reflection mirror 24, on the light-incident end surface of the light guide 15. In addition, with the DMD 23, if the micromirror is then set to take an angle of +10°, the mirror, upon receiving incoming light from the parabolic mirror 22, reflects it in a direction so much diverted from the preceding one that the light will not impinge on the reflection mirror 24. In other words, the DMD 23 controls the supply of illuminating light to the light-incident end surface of the light guide 15 by permitting illuminating light from the light source lamp 21 to impinge on the reflection mirror 24 or not.

This embodiment is configured such that the system determines the type of CCD 2a based on the information provided by the CCD-type determining element 14, controls the DMD 23 based on the determination result, and adjusts the time during which illuminating light is shielded, depending on the type of the CCD 2a.

The video processor 4 comprises a CPU control portion (referred to as CPU, hereinafter) 31 which determines the type of CCD based on the information provided by the CCD-type determining element 14, and detects the time the CCD requires for reading charge; a timing generator (referred to as TG, hereinafter) 32 which provides a read-out timing appropriate for the CCD2a incorporated in the endoscope 2 in accordance with the charge reading time determined by the CPU 31, as well as a processing timing in synchronization with the read-out timing; a CCD driver 33 which drives the CCD 2a in accordance with the read-out signals provided by the TG 32; a pre-process circuit 34 which applies processing such as CDS (correlation-based dual sampling) to the image pickup signals from the CCD 2a; an A/D converter circuit 35 which converts image pickup signals existing as analog signals provided by the pre-process circuit 34 into digital signals; an image pickup signal processor 36 which processes image pickup signals which have been digitized by the A/D converter circuit 35 into video signals; a coincidence circuit 37 which sequentially stores video signals which have undergone signal processing at the image pickup signal processor 36 into a plurality of coincidence memories not illustrated here and which performs synchronization of the frame-sequential images by synchronously reading out the stored video signals; a γ correction circuit 37 which applies γ correction to video signals coming from the coincidence circuit 37; and a D/A converter 38 which converts digital video signals having received γ correction at the γ correction circuit 37 into analog signals.

The video processor 4 further comprises a light adjustment circuit 41 which controls the aperture 26 of the light source apparatus 5 and the motor 29 responsible for activating the rotational filter plate 27 in correspondence with image pickup signals digitized by the A/D converter 35 based on the processing timing provided by the TG 32, and a DMD control circuit 42 which controls the DMD 23 of the light source apparatus 5 in accordance with the read-out timing of the CCD 2a provided by the TG 32.

Next, the operation of the endoscope system 1 configured as above will be described.

Firstly, the operator connects the connector portion 13a of the endoscope 2 to the light source apparatus 5 and the video processor 4, and switches on the power for endoscopic examination.

The CPU 31 determines the type of CCD based on the information provided by the CCD-type determining element 14, and the time that the CCD 2a requires for reading charge. The TG 32 generates timing clocks appropriate for the CCD 2a to read charge, and processing timing clocks in synchronization with the read-out clocks, in accordance with the charge reading time determined by the CPU 31.

Light radiated from the light source lamp 21 of the light source apparatus 5 impinges on the parabolic mirror 22, is then reflected by DMD 23, passes through the reflection mirror 24, the integrator 25, the aperture 26, and the rotational filter plate 27, and is converged by the converging lens 28 onto the light-incident end surface of light guide 15. During this process, the DMD control circuit 42 controls the DMD 23 in accordance with the read-out clocks for the CCD 2a provided by the TG 32.

Further, the light adjustment circuit 41 delivers an aperture control signal to the aperture 26 in accordance with the processing timing provided by the TG 32 so that an image reproduced from image pickup signals digitized by the A/D converter circuit 35 may have an appropriate brightness. The aperture 26, in response to the aperture control signal delivered by the light adjustment circuit 41 of the video processor 4, restricts the quantity of light emanating from the light source apparatus 5, so as to prevent an image reproduced by the CCD 2a from being over-saturated. The light adjustment circuit 41 further controls the motor 29 for driving the rotational filter plate 27 in accordance with the processing timing provided by the TG 32 so that the filter may be driven into rotation at a specified rotational speed. When the rotational filter plate 27 is driven into rotation by the motor 29, the R filter sector 27a, the G filter sector 27b, and the B filter sector 27c intercept the light path sequentially in this order so as to permit the passage of red, green, and blue light, respectively.

Light entering the light guide 15 of the endoscope 2 is radiated from the tip 11a of the insertion segment 11 onto a test object, such as the digestive tract. Beams scattered or reflected by the test object are focused onto the surface of the CCD 2a, which is fixed in the tip 11a of the insertion segment 11. The CCD 2a, being driven by the CCD driver 33 in synchronization with the rotation of the rotational filter plate 27 based on timing signals provided by the TG 32, delivers image pickup signals of the test object illuminated in succession by light components sequentially having passed through the R, G and B filter sectors 27a, 27b, and 27c of the rotational filter plate 27 or the like to the video processor 4. Alternatively, a rotation position detecting means for detecting the rotation position of the rotational filter plate 27 may be introduced, and the CCD driver 33 may be driven in synchronization with the rotation of the rotational filter plate 27 based on its rotation position detected by the rotation position detecting means.

Image pickup signals provided to the video processor 4 first enter the pre-process circuit 34 where they undergo CDS (correlation-based dual sampling) processing or the like, and then undergo A/D conversion via the A/D converter circuit 35. The digitized image pickup signals are processed into video signals by the image pickup signal processor 36, and are then sequentially stored in a plurality of coincidence memories (not illustrated here). The coincidence circuit 37 simultaneously reads the video signals which have been sequentially stored into the plurality of coincidence memories, thereby achieving coincident unification of the sequential video signals. The sequential video signals thus coincidentally unified receive a γ correction at the γ correction circuit 37, and are converted by the D/A converter circuit 38 into analog signals, to be delivered to the monitor 3.

If the endoscope incorporates a CCD 2a with a relatively small number of pixels which will require a relatively short time for charge reading, the DMD control circuit 42 controls the DMD 23 in such a manner as to reduce the time for light shielding, as shown in FIG. 3. For example, in this particular example, the exposure time for R, G, or B is 13 ms and the light shielding time is 4 ms.

In contrast, if the endoscope incorporates a CCD 2a with a relatively large number of pixels which will require a relatively long time for charge reading, the DMD control circuit 42 controls the DMD 23 in such a manner as to extend the time for light shielding, as shown in FIG. 4. For example, in this particular example, the exposure time for R, G, or B is 10 ms and the light shielding time is 7 ms.

During the R, G, or B exposure time, each of the micromirrors of the DMD 23 is controlled by the DMD control circuit 42 to take an angle to guide illuminating light from the light source lamp 21 to the light-incident end surface of light guide 15. On the other hand, during the light shielding time, each of the micromirrors of the DMD 23 is controlled by the DMD control circuit 42 to take an angle to guide illuminating light from the light source 15 away from the light-incident surface of light guide 15.

As a consequence, according to the endoscope system 1 representing the present embodiment of the present invention, even if a CCD 2a requiring a different time for charge reading and thus a different time for light shielding is attached to the endoscope 2, it is possible to ensure the longest exposure time attainable with that type of CCD 2a.

It should be noted, however, that the present invention is not limited to the above embodiments, and various variants thereof are possible without departing from the spirit of the present invention.

Note that the conventional light source apparatus wherein the distribution of illuminating light from the light source lamp 21 can be modified includes, for example, one that is described in Japanese Unexamined Patent Application Publication No. 4-297225 wherein liquid crystal is used as a light modulation device.

However, the light source apparatus incorporating liquid crystal as a light modulation device is problematic in that the usage efficiency of light is reduced because light will be absorbed by frames between adjacent liquid crystal pixels.

In view of this, there has been a need for a light source apparatus which can illuminate with light having a desired spectroscopic distribution with high efficiency.

Figures 5A, 5B:
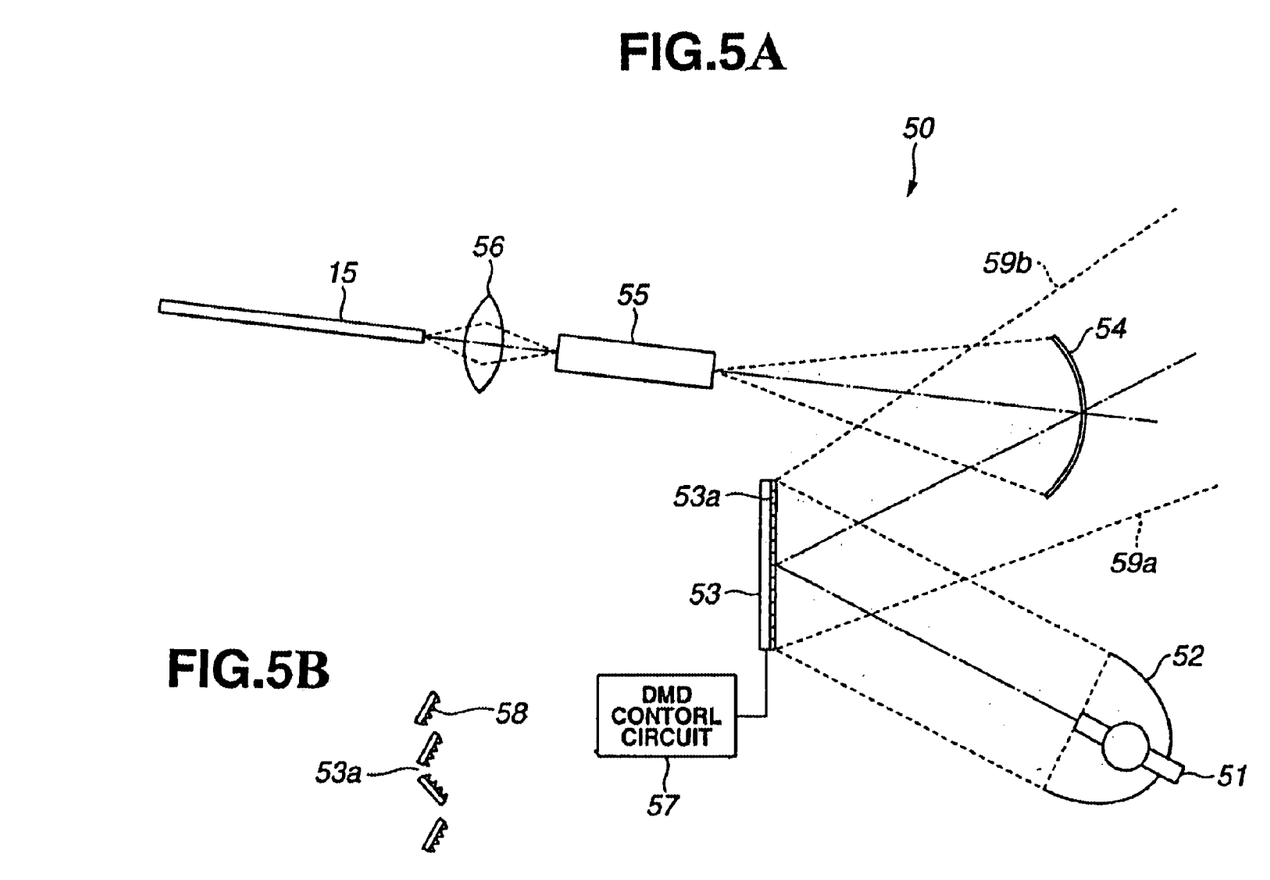
FIG. 5A is an illustration showing the optical system of a light source apparatus incorporating a DMD having a spectroscopic reflecting film formed thereon.
FIG. 5B is an outline for micromirrors of the DMD in FIG. 5A each having a spectroscopic reflecting film coated in its reflecting surface.
Figure 6:
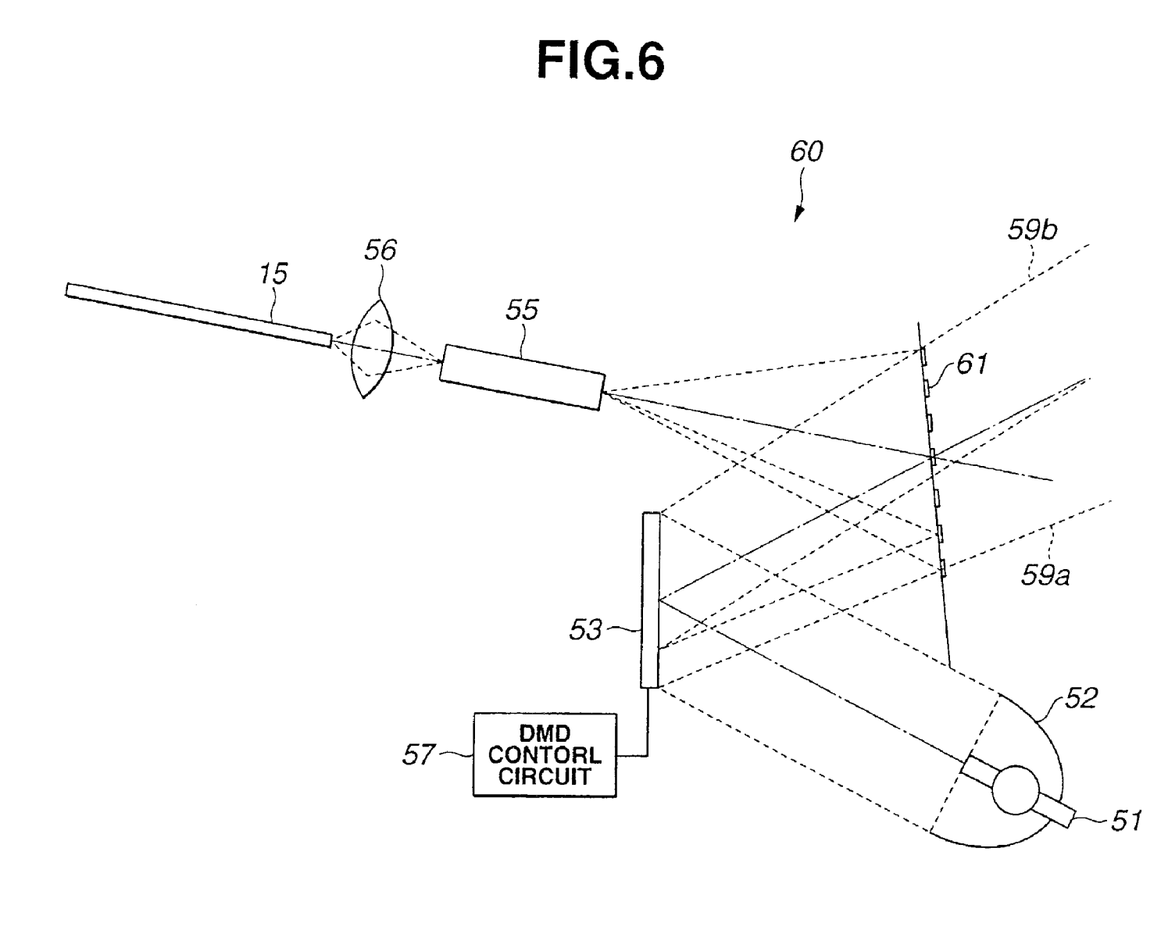
FIG. 6 is an illustration showing the optical system of a light source apparatus incorporating a reflection mirror having a reverse dispersion function.
Figure 7:
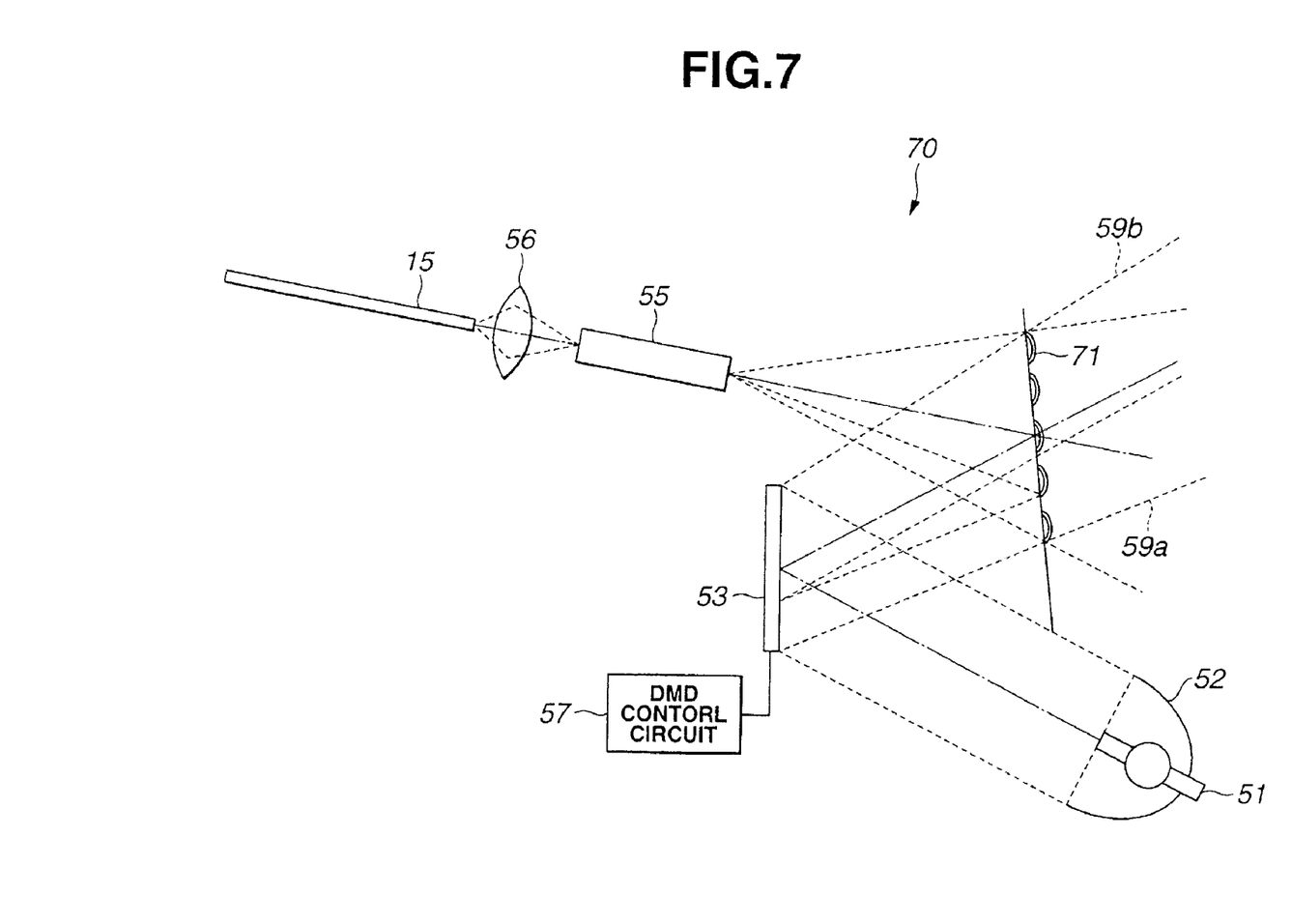
FIG. 7 is an illustration showing the optical system of a light source apparatus which incorporates individually separated reflection mirrors.
Figure 8:
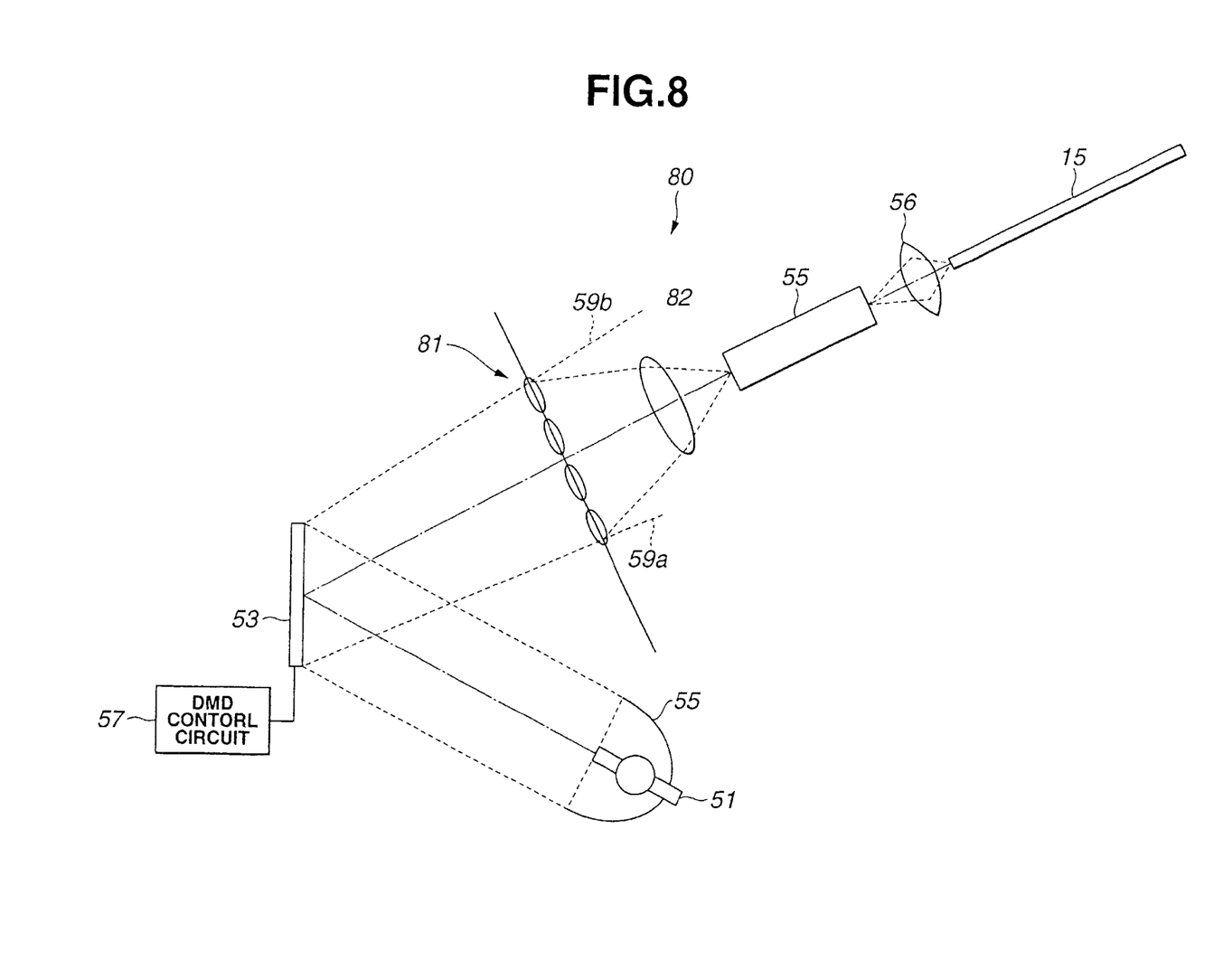
FIG. 8 is an illustration showing the optical system of a light source apparatus which incorporates groups of lenses for combining beams reflected from a DMD.

Examples of the constructions of light source apparatuses will be explained with reference to FIGS. 5 to 8. FIGS. 5 to 8 concern the examples of the constructions of light source apparatuses: FIG. 5 illustrates the construction of a light source apparatus incorporating a DMD as a light modulating device, i.e., FIG. 5(A) illustrates the optical system of a light source apparatus incorporating a DMD having a spectroscopic reflecting film formed thereupon, and FIG. 5(B) outlines the micromirrors of the DMD in FIG. 5A each having a spectroscopic reflecting film coated on its reflecting surface; FIG. 6 illustrates the optical system of a light source apparatus incorporating a reflection mirror having a reverse dispersion function; FIG. 7 illustrates the optical system of a light source apparatus incorporating individually separated reflection mirrors; and FIG. 8 illustrates the optical system of a light source apparatus incorporating groups of lenses for combining beams reflected by the DMD.

The optical system 50 of the light source apparatus shown in FIG. 5(A) has practically the same construction as that of the light source apparatus 5 described above, and it comprises a light source lamp 51, such as a Xenon lamp or the like, which radiates light to be provided to the endoscope (not illustrated here); a parabolic mirror 52 which has its surface coated to filter out infra-red rays, so as to remove infra-red components from the light emanating from the light source lamp 51; a DMD (Digital Micromirror Device) 53 which restricts parallel beams from the parabolic mirror 52 in the time domain; a reflection mirror 54 for reflecting a part of radiation light radiated by the DMD 53; an integrator 55 for integrating beams reflected by the reflection mirror 54; and a converging lens 56 which converges the beams uniformly integrated by the integrator 55 onto a light-incident end surface of the light guide 15.

The DMD 53 is an element obtained by arranging a matrix of 800×600 micromirrors each supported by a support member on a silicon chip over a yoke which moves between two stable states, with one diagonal line as a pivot, so that the mirrors can move in a horizontal direction within an angular range of ±10° independently of each other. Each micromirror 53a of the DMD 53 is controlled by the DMD control circuit 57 such that the micromirrors are independently controlled. The DMD 53 is arranged with respect to incident light from the parabolic mirror 52 such that, if, for example, a micromirror is set to take an angle of −10°, illuminating light reflected by the micromirror 53a will impinge, via the reflection mirror 54, on the light-incident end surface of the light guide 15. In addition, with the DMD 53, if the micromirror 53a is then set to take an angle of +10°, the mirror, upon receiving incoming light from the parabolic mirror 52, reflects it in a direction so much diverted from the preceding one that the light will not impinge on the reflection mirror 54.

In this example, as shown in FIG. 5(B), each micromirror 53a of the DMD 53 has a diffracting/reflecting surface 58 which diffracts light impinging thereupon. This arrangement allows each micromirror 53a of the DMD 53 to reflect an incident beam at a different angle depending on its wavelength. Thus, beams reflected therefrom vary in an angular range of ±10° depending on the angle of the micromirror upon which they impinge, with an additional diffraction component depending on their wavelength.

Next, the operation of the optical system of the light source apparatus constructed as above will be described.

Light radiated by the light source lamp 51 impinges, via the parabolic mirror 52, onto the DMD 53. Light-incident onto the DMD 53 is diffracted and reflected by the diffracting/reflecting surface 58 of micromirrors 53a, to be transmitted to the reflection mirror 54. Some of the reflected beams will not impinge on the reflection mirror 54 because the reflected angles of those beams differ depending on their wavelength.

When a given micromirror 53a of the DMD 53 is set to take an angle of ±10°, it will reflect light in a direction indicated by 59a in the figure. On the other hand, when the micromirror 53a of the DMD 53 is set to take an angle of −10°, it will reflect light in a direction indicated by 59b in the figure. Thus, it is possible to determine whether or not a given beam is reflected by reflection mirror 54 by altering the angle of the micromirror upon which the beam impinges in a range of ±10°. As is obvious from this, it is possible by adjusting the angle of the mirrors on the DMD 53 to alter the light flux reflected by the reflection mirror 54, or to control the relative contribution of beams of different wavelengths contained in the reflected light.

The DMD 53 can give light with a desired distribution (spectroscopic distribution) of beams with different wavelengths by adjusting the angle of individual micromirrors 53a in a range of ±10/−10. Namely, light reflected by the reflection mirror 54 can be used as endoscopic illumination whose color can be freely altered.

As a consequence, according to the light modulation device of this embodiment, it is possible to provide illuminating light which has a desired spectral distribution, so as to achieve more effective illumination, that is, to more efficiently illuminate a test object than is possible with the liquid crystal-based device.

The optical system 60 of a light source apparatus shown in FIG. 6 incorporates a plurality of reflection mirrors 61 each having a reverse dispersion function, to cause beams having different wavelengths to be reflected at different angles.

Because of this, beams reflected by the plurality of reflection mirrors 61 take various angles depending on their wavelength. The beams separated by wavelength are then merged by wavelength to be incident on the integrator 55. The reflection mirror consists of either reflecting surfaces or transparent surfaces arranged in concentric rings. This allows the light reflected by a given mirror at a certain mirror angle to be incident on the integrator 55 depending on its wavelength.

This ensures the same advantage as in the optical system 50 of the light source apparatus described with reference to FIG. 5.

The optical system 70 of another light source apparatus as shown in FIG. 7 is so constructed as to selectively reflect beams reflected by the DMD 53.

To achieve this purpose, the system is constructed such that, beams reflected by mirrors of the DMD 53 at respective angles are selected by a plurality of reflection mirrors 71 according to their wavelengths, to be incident onto the integrator 55.

This construction ensures the same advantage as in the optical system 50 of the light source apparatus described with reference to FIG. 5.

The optical system 80 of a still another light source apparatus shown in FIG. 8 is constructed such that beams reflected by DMD 53 are selectively incident onto the integrator 55 via a plurality groups of lenses 81.

Beams passing through the groups of lens 81 are converged by a converging lens 82 onto the integrator 55.

This ensures the same advantage as in the optical system 50 of the light source apparatus described above with reference to FIG. 5.

Incidentally, the conventional light source apparatus has adopted a monochromator or a plurality of narrow-band filters arranged on a turret which can be rotated to intercept the light path from a light source lamp, as means to freely select and illuminate beams by their wavelength.

However, although it allows the selection of beams with a continuously varying wavelength, the monochromator is problematic because with it the alteration of wavelength occurs slowly. On the other hand, the narrow-band filters, the wavelengths to be selected are limited, although the scanning speed is relatively high.

To deal with these problems, there has been a demand for a light source apparatus which can alter the wavelength of illuminating light continuously and selectively at high speed.

Figure 9:
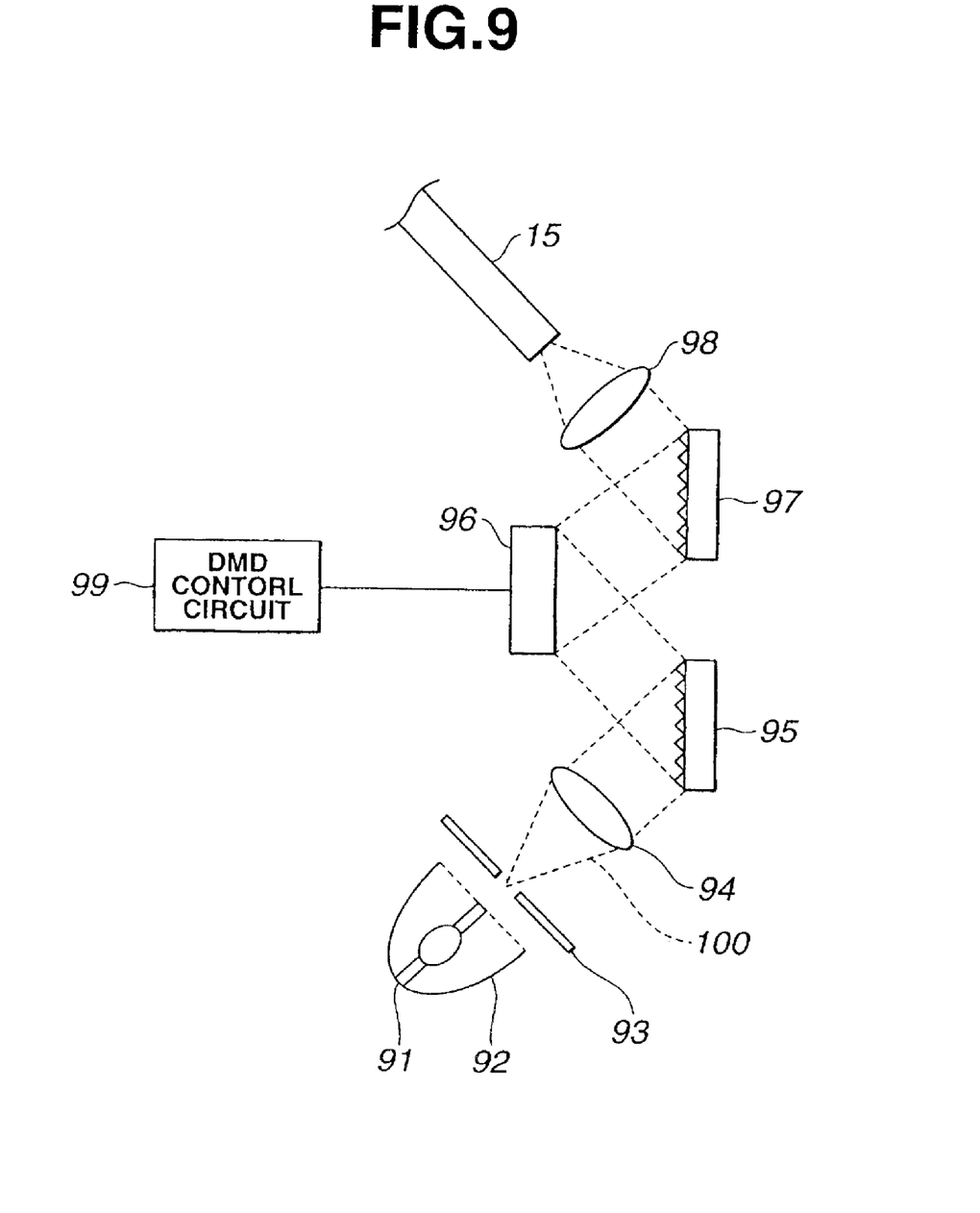
FIG. 9 is an illustration showing the optical system of a light source apparatus which incorporates a DMD as a light modulating device.
Figure 10:
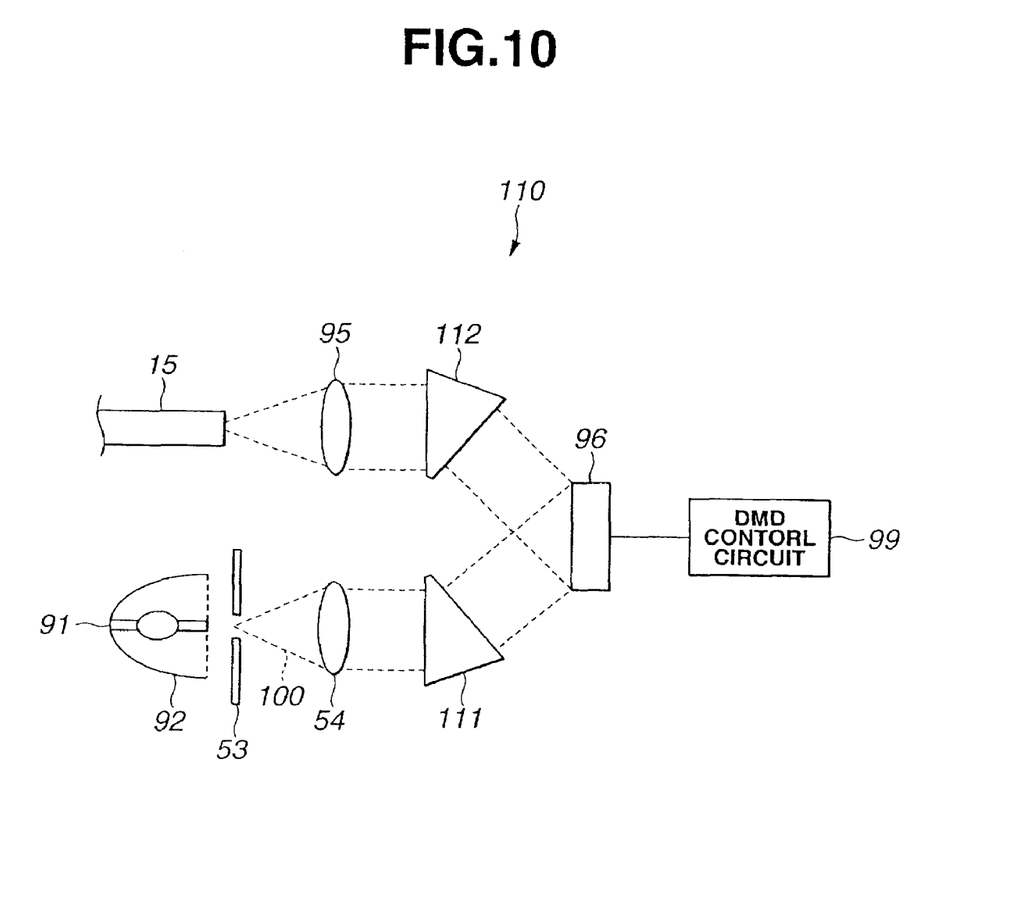
FIG. 10 is an illustration showing a variant of the apparatus of FIG. 9.

The construction of still another light source apparatus will be described with reference to FIGS. 9 and 10. FIGS. 9 and 10 concern the construction of a light source apparatus: FIG. 9 illustrates the optical system of a light source apparatus incorporating a DMD as a light modulating device, while FIG. 10 illustrates a variant of the apparatus of FIG. 9.

As shown in FIG. 9, the optical system 90 of the light source apparatus comprises a light source lamp 91; a spherical mirror 92 for reflecting light radiated by the light source lamp 91; a slit 93 placed close to the light source lamp 91; a first lens 94 which converts the light flux passing through the slit 93 into a parallel beam; a first diffraction grating 95 which diffracts light fluxes 100 emanating from the first lens 94 for dispersion; a DMD 96 which selectively reflects beams dispersed by the first diffraction grating 95 by altering the direction of micromirrors arranged in an array; a second diffraction grating 97 which diffracts light selectively reflected by the DMD 96 for reverse dispersion; and a second lens 98 which converges beams reflected and reversely dispersed by the second diffraction grating 97 onto a light guide 15. The micromirrors of DMD 96 are designed so as to be independently controlled by the DMD control circuit 99.

Next, the operation of the optical system of the light source apparatus configured as above will be described.

Light emanating from the light source lamp 91 passes through slit 93 directly or after having been reflected by the spherical mirror 92. Light passing through slit 93 is converted by the first lens 94 into a parallel beam which then impinges upon the first diffraction grating 95.

The beam incident on the first diffraction grating 95 is diffracted and reflected by the first diffraction grating 95. Light fluxes 100 thus reflected, being dispersed as a result of the dispersing activity characteristic with the diffraction grating, are incident on the DMD 96.

Because light fluxes 100 incident on the DMD 96 are dispersed with respect to the incident direction, it is possible to selectively allow desired light components to be incident on the second diffraction grating 97 by adjusting the angle of the mirror which will receive a beam with a wavelength that is desired to enter the light guide 15.

Light fluxes 100 with a desired wavelength which have been selected by the DMD 96 to be incident on the second diffraction grating 97 are reversely dispersed by the second diffraction grating 97 to be incident on the second lens 98, and then converged to the end surface of the light guide 15.

As a consequence, according to this embodiment, it is possible to scan the wavelength of light incident on the light guide 15 at high speed. Because of this, according to this embodiment, it is possible to realize very fast endoscopic, spectroscopic imaging which will lead to the improvement of diagnostic performance. Further, according to this embodiment, because it is possible to realize very fast sequential replacement of two dimensional images, the quality of images will be improved even when the embodiment is used as a substitutive means for sequential two dimensional filters.

Moreover, because the above embodiment allows a beam with a single wavelength or beams with different wavelengths to be selected, it is possible to apply the system to the multiple endoscopic diagnoses such as fluorescent imaging, vascular imaging based on a light absorbing agent, measurement of the oxygen saturation of hemoglobin, etc., and thus to improve the endoscopic diagnostic performance.

With regard to the optical system 110 of the light source apparatus, the first and second diffraction gratings 95 and 97 may be substituted for prisms, as shown in FIG. 10.

More specifically, the optical system 110 of the light source apparatus has its first and second diffraction gratings 95 and 97 substituted for first and second prisms 111 and 112, respectively, to allow light fluxes 100 to pass through those prisms. This arrangement allows the first and second prisms 111 and 112 to serve respectively as light dispersing elements.

As a consequence, in addition to the advantages obtained from the optical system 90 of the light source apparatus described with reference to FIG. 9, it is possible to provide intense incident light to the light guide 15 because the light transmission efficiency is higher with the prisms than with the diffraction gratings.

Having described the preferred embodiments of the invention by referring to the accompanying drawings, it should be understood that the present invention is not limited to those precise embodiments, and various changes and modifications thereof could be made by one skilled in the art without departing from the spirit or scope of the invention as defined in the appended claims.

What is claimed is:

1. A light source apparatus for providing illuminating light to an endoscope, comprising:
   a light source lamp for generating illuminating light;
   a digital micromirror device having a plurality of micromirrors which receive and reflect the illuminating light generated by the light source lamp, wherein each of the plurality of micromirrors rotates to change a reflection direction of said illuminating light;
   a light-converging optical system for directing the illuminating light reflected by the plurality of micromirrors to be incident on a light guide integrated in the endoscope;
   a mirror control circuit which determines whether or not the illuminating light should impinge on the light guide integrated in the endoscope by altering the direction of the illuminating light reflected by the plurality of micromirrors of the digital micromirror device based on an exposure-time control signal introduced in accordance with the type of an imaging element installed in the endoscope;
   a mirror which reflects an incident light component out of light reflected by the digital micromirror device towards the light guide introduced in the endoscope; and
   a light integrating device for uniformly integrating the reflected light inserted between the mirror and the light-converging optical system.

2. A light source apparatus of claim 1 wherein:
   the mirror control circuit controls the supply of illuminating light to the light guide by altering the direction of the illuminating light reflected by the plurality of micromirrors, based on the exposure-time control signal introduced in accordance with a time required for charge reading corresponding with the number of pixels of the imaging element installed in the endoscope.

3. A light source apparatus of claim 2 wherein:
   the mirror control circuit controls the plurality of micromirrors of the digital micromirror device based on a read-out timing of the imaging element provided by a timing generator which provides a processing timing in synchronization with the charge reading time corresponding to the number of pixels of the imaging element.

4. A light source apparatus of claim 1, wherein the digital micromirror device comprises:
   driving means which determines the incidence or non-incidence of the illuminating light on the light guide introduced in the endoscope by driving the plurality of micromirrors.

5. A light source apparatus of claim 1 wherein:
   an optical filter is introduced such that it periodically intercepts a light path between the mirror and the light-converging optical system to allow, out of the illuminating light, light components with a limited range of wavelengths to pass through.

6. A light source apparatus of claim 5 wherein:
   the optical filter is a rotational filter obtained by arranging a plurality of sectors around the center, each defining a region which can filter light components with a specified range of wavelengths.

7. A light source apparatus of claim 5 wherein:
   the mirror control circuit controls the supply of illuminating light to the light guide by altering the direction of illuminating light reflected by the digital micromirror device based on the exposure-time control signal introduced in accordance with a time required for charge reading corresponding to the number of pixels of the imaging element installed in the endoscope, the control comprising reducing a time for light shielding when the number of pixels of the imaging element is so small that charge reading will be completed in a short time, and extending the time for light shielding when the number of pixels of the imaging element is so large that charge reading will take a long time.

8. An endoscope system for enabling endoscopic observation by providing illuminating light to an endoscope, comprising:
   a light source lamp for generating illuminating light;
   digital micromirror device having a plurality of micromirrors which receive and reflect the illuminating light generated by the light source lamp, wherein each of the plurality of micromirrors rotates to change a reflection direction of said illuminating light;
   a light guide which is capable of transmitting the illuminating light and which is installed in the endoscope;
   a light-converging optical system for directing the illuminating light reflected by the plurality of micromirrors of the digital micromirror device to be incident on the light guide;
   an imaging element installed in the endoscope;
   a type determining circuit for determining the type of the imaging element;
   a control signal generating circuit which generates an exposure-time control signal responsible for controlling the exposure time of the imaging element in accordance with the type of the imaging element determined by the type determining circuit; and
   a mirror control circuit which determines whether or not the illuminating light should impinge on the light guide introduced in the endoscope by altering the direction of the illuminating light reflected by the plurality of micromirrors of the digital micromirror device based on the exposure-time control signal generated by the control signal generating circuit;
   a mirror which reflects an incident light component out of light reflected by the digital micromirror device towards the light guide introduced in the endoscope; and
   a light integrating device for uniformly integrating the reflected light inserted between the mirror and the light-converging optical system.

9. An endoscope system of claim 8 wherein:
   the imaging element is installed within a tip of an insertion segment of the endoscope.

10. An endoscope system of claim 8 wherein:
    the type determining circuit for determining the type of imaging element determines the type of imaging element installed in the endoscope and detects the time required by the imaging element for charge reading.

11. An endoscope system of claim 10 wherein:

the mirror control circuit determines whether or not the illuminating light should impinge on the light guide by altering the direction of the illuminating light reflected by the plurality of micromirrors of the digital micromirror device based on the exposure-time control signal introduced in accordance with a charge reading time corresponding to the number of pixels of the imaging element detected by the type determining circuit.

12. An endoscope system of claim 10 wherein:

the mirror control circuit controls the plurality of micromirrors of the digital micromirror device based on an imaging element read-out timing provided by a timing generator which provides a processing timing in synchronization with the charge reading time corresponding to the number of pixels of the imaging element.

13. An endoscope system of claim 10 wherein:

an optical filter is introduced such that the optical filter periodically intercepts a light path between the mirror and the light-converging optical system to control the passage of illuminating light, thereby allowing light components with a specified wavelength to pass through.

14. An endoscope system of claim 13 wherein:

the mirror control circuit controls the supply of illuminating light to the light guide by altering the direction of the illuminating light reflected by the digital micromirror device based on the exposure-time control signal introduced in accordance with a time required for charge reading corresponding to the number of pixels of the imaging element installed in the endoscope, the control comprising reducing a time for light shielding when the number of pixels of the imaging element is so small that charge reading will be completed in a short time, and extending the time for light shielding when the number of pixels of the imaging element is so large that charge reading will take a long time.

* * * * *